United States Patent [19]

Enger

[11] 4,011,861

[45] Mar. 15, 1977

[54] IMPLANTABLE ELECTRIC TERMINAL FOR ORGANIC TISSUE

[75] Inventor: Carl C. Enger, Lakewood, Ohio

[73] Assignee: Case Western Reserve University, Cleveland, Ohio

[22] Filed: Oct. 28, 1975

[21] Appl. No.: 626,191

Related U.S. Application Data

[63] Continuation-in-part of Ser. No. 457,467, April 3, 1974, abandoned.

[52] U.S. Cl. .................... 128/2.06 E; 128/2.1 E; 128/DIG. 4; 128/418; 128/419 P; 128/419 C; 128/419 E; 128/419 F

[51] Int. Cl.$^2$ ............... A61B 5/04; A61N 1/04

[58] Field of Search .......... 128/418, 419 P, 419 B, 128/419 C, 419 D, 419 E, 419 F, 404, 2.06 E, 2.1 E, DIG. 4; 3/1

[56] References Cited

UNITED STATES PATENTS

| | | | |
|---|---|---|---|
| 3,314,420 | 4/1967 | Smith et al. ................ | 128/92 R |
| 3,345,989 | 10/1967 | Reynolds .................. | 128/419 P |
| 3,596,662 | 8/1971 | Bolduc ..................... | 128/418 |
| 3,663,965 | 5/1972 | Lee et al. .................. | 3/1 |
| 3,737,579 | 6/1973 | Bolduc ..................... | 128/418 |
| 3,752,162 | 8/1973 | Newash .................... | 128/419 P |

OTHER PUBLICATIONS

B535,466, Jan. 1976, Cannon, 128/419 P.
Guyton et al., "Capacitor Electrode . . . Reactions," Science, vol. 181, pp. 74–76, July, 1973.
Trimble, "Clinical Engineering," Medical Instrumentation, vol. 8, No. 2, Mar.–Apr., 1974.
Gertler, "Interface for Passing Lead Wires . . . Animals," IEEE Trans. on Bio-Med. Eng'g, vol. 18, No. 1, Jan. 1971.

Cassel et al., "Implanted Ag-AgCl Mag. Power Sources," Med. Inst., vol. 7, No. 3, May–Aug., 1973, pp. 176–179.
Becker et al., "Electrical Stimulation of Hard Tissue Growth . . . Devices," Oct. 30, 1973.

*Primary Examiner*—Robert W. Michell
*Assistant Examiner*—Lee S. Cohen

[57] ABSTRACT

A non-reacting implantable electric terminal for organic tissue, which is porous and intermeshes with the tissue including blood capillaries without the formation of a fibrous tissue encapsulation that reduces the sensitivity of tissue to electricity. This electric terminal is composed of tissue-compatible implantable material or materials at least one of which is electrically conductive, such as platinum, or an alloy, and which has on at least one surface thereof a porous material or layer having pores that are interconnected and continuous so that body electrolytes and/or tissue containing blood capillaries can contact the electrically conductive material through said porous material or layer. The pores of this material or layer also must have an average diameter sufficient to permit blood vessels to form in them, i.e. a diameter preferably between about 10 and 500 microns. This porous material may be either electrically conductive or electrically non-conductive, and may comprise a porous metal, carbon, ceramic, such as one containing aluminum oxide, and/or a synthetic polymer, or elastomer, such as one containing a silicone, a fluorocarbon, or an epoxy resin. The shape of the electric terminal may vary as desired, and the more interconnected pores it contains the better. This electric terminal may either be placed on the surface of the tissue like a plate or disk, or be inserted into the tissue.

26 Claims, 7 Drawing Figures

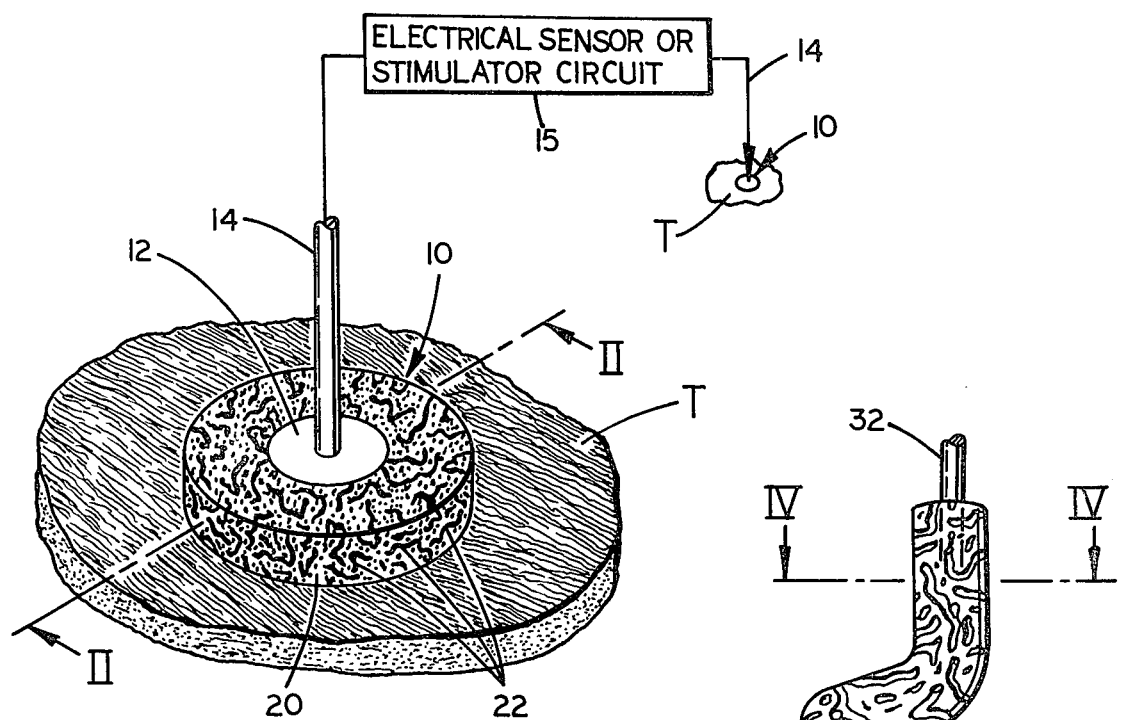
FIG. I
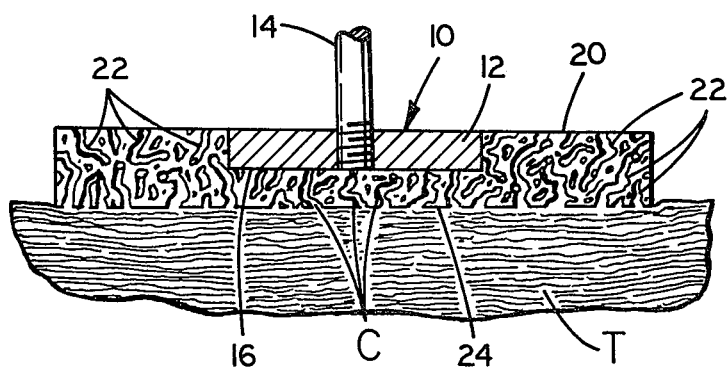
FIG. II
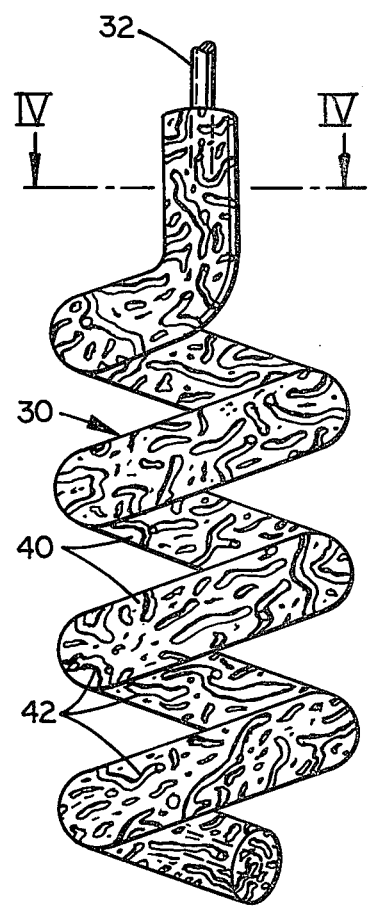
FIG. III

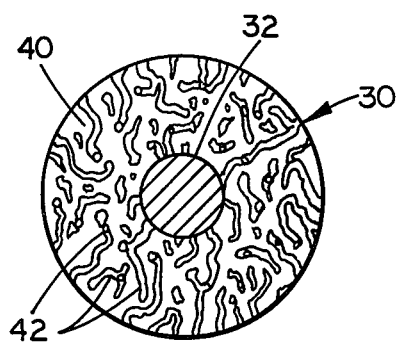
FIG. IV
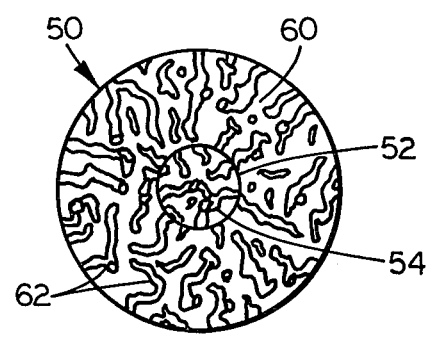
FIG. V
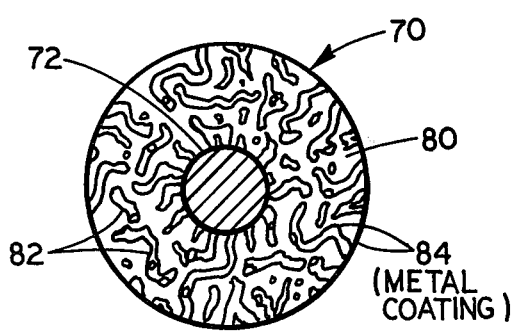
FIG. VI
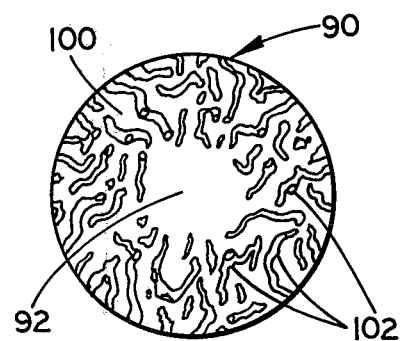
FIG. VII

IMPLANTABLE ELECTRIC TERMINAL FOR ORGANIC TISSUE

RELATED APPLICATIONS

This is a continuation-in-part application of applicant's copending application Ser. No. 457,467 filed Apr. 3, 1974 entitled "Implantable Electrode For Organic Tissue," now abandoned.

BACKGROUND OF THE INVENTION

When inert foreign bodies such as metals, ceramics, plastics, or the like, are implanted or contacted with living tissue, such as in an animal or the human body, the living tissue builds up a defensive fibrosis around this body in an effort to reject, insulate and isolate it from the vascularized tissue. In the case of electric terminals or electrodes, particularly those for stimulation for heartpacers as described in applicant's U.S. Pat. No. 3,659,615, issued May 2, 1972, its metal electrodes puncture the myocardium and soon become coated with fibrous tissue reducing the electrical conductivity into the muscle.

L. W. Smith et al in their U.S. Pat. No. 3,314,420 issued Apr. 18, 1967 disclosed a porous ceramic material as a bone substitute into which body tissue grows.

F. W. Rhinelander et al in their article entitled "Microvascular and Histogenic Responses To Implantation Of A Porous Ceramic Into Bone" published in J. Biomed. Mater. Res. Vol. 5 pp 81–112 (1971) disclosed that bone tissue containing blood capillaries grew deep into and intermeshed with the porous ceramic materials patented by Smith et al. Furthermore, S. F. Hulbert et al in their article entitled "Compatibility Of Porous Ceramic With Soft Tissue; Application To Tracheal Prothesis" published in J. Biomed. Mater. Res. Symposium Vol. 2 (part 1) pp 267–279 (1971) disclosed that soft tissue containing blood capillaries also grew deep into the interconnecting pores of porous ceramics.

R. B. Beard et al in their article entitled "Porous Cathodes For Implantable Hybrid Cells" published in the I.E.E.E. Transactions on Biomedical Engineering, Vol. 19, No. 3 May 1972, disclosed that porous platinum and palladium black catalystic electrodes for power generation when implanted in soft tissue produced a surrounding tissue capsule having apparent revascularization in said capsule, and that there were some apparent tissue ingrowth into the pores of the electrodes which caused poisoning of its catalytic effect. Furthermore, the formation of a granulated or fibrous tissue around implanted active porous electrodes, such as for fuel cells, was disclosed into the Drake et al article entitled "A Tissue Implantable Fuel Cells Power Supply" published in Vol. XVI Trans. Actions American Soc. Artif. Int. Organs 1970 pp 199–205.

Accordingly, the problem was to produce a non-reacting implantable electric terminal without the formation of a fibrous tissue coating.

SUMMARY OF THE INVENTION

Generally speaking the non-reacting implantable electric terminal of this invention comprises a substrate of an electrically conductive porous or non-porous material, such as metal in the form of a flat disk or a wire or other shape, to which is intimately attached an inert non-absorbable porous material, such as a layer, either of the same or of a different composition which may be an electrically conductive or an electrically non-conductive porous material, such as a metal, carbon, ceramic, metal plated ceramic, plastic, metal plated plastic, or a combination thereof. This porous material is provided with sufficient pores so that at least some of them are interconnected and continuous throughout its thickness to the electrically conductive material or part of this electric terminal. These pores are of a sufficient size so as to permit blood vessels to form in them from the tissue or in which the porous material is implanted, but small enough to prevent the formation of fibrosis therein. Also these pores must permit the body electrolytes to fill these passages for conducting the electricity from the electrically conductive part of this electric terminal into the tissue.

The electrically conductive material or substrate of this electric terminal preferably is a inert porous or non-porous material and must be compatible to the body tissue and body fluids in which it is implanted. Such materials include, for example: platinum, iridium, niobium, indium, paladium, titanium, tantalum, vanadium, tungsten, chromium, cobalt, stainless steel, an alloy of some of these metals called Vitallium or Elgiloy, carbon, or the like. These materials may be formed into various shapes for intimate contact or implantation in or onto the particular tissue which is to be stimulated or sensed.

The porous layer or coating on the electrically conductive part of this electric terminal occurs at least upon the surface which is in contact with the tissue to be sensed or stimulated, and preferably all of its surface not to be electrically insulated from the tissue. This porous layer may comprise either a porous layer of the same or other electrically conductive material, or may comprise a coating of a non-electrically conductive porous material. These porous materials may range from 5% to 85% porous in which a sufficient number of the pores interconnect and are continuous so that the layer is easily permeable to the electrolytes in the organic tissue.

The size of the pores may vary anywhere between about 0.5 microns in diameter up to about 1000 microns, however, it has been found that pores whose average diameters fall within the range of about 10 and 500 microns are most satisfactory. The pore sizes must be sufficient for the blood vessels and tissue to grow into them for better intimate contact with the tissue to be electrically sensed or stimulated.

If this porous layer is of an electrically conductive material, it may be of metal, carbon, a metal plated or coated non-conductive material, an electrically conductive plastic which may contain metal, and/or carbon, or it may be same material as the substrate of the electric terminal. These electrically conductive materials also may be combined with a ceramic to form a porous permeable layer of the implantable electric terminal of this invention.

If this porous layer is of an electrically non-conductive material, it may be of a ceramic or metallic oxide, such as aluminum oxide, silicon dioxide, or either or both of these oxides together with calcium, magnesium, titanium and/or zirconium oxides, or a porous ceramic of such oxides called Cerosium.

This porous layer also may comprise a plastic material, such as a natural or synthetic polymer or elastomer, such as for example a silicone, a fluorocarbon, an epoxy resin, nylon, a rubber, polyurethane, polyethylene, polypropylene, polycarbonate, or mixtures thereof preferably that are compatible with and implantable into organic tissues and fluids. These plastics also may be combined with a ceramic to form the porous permeable layer of the implanted electric terminal of this invention.

If the only electrical contact with the electric terminal is at the end of the continuous pores in the electrical non-conductive coating layer, the current density is greater for that electric terminal than it would be if its core or electrical conductive part were also porous, and/or if the porous coating layer were also electrically conductive, such as being made out of an electrically conductive porous material or out of an electrically non-conductive porous material coated or plated with an electrically conductive material, such as a non-reacting metal.

The implantable electric terminals of this invention are effective for use as sensors and/or stimulators for the heart, for the bladder, the pancreas, the central nervous system, the carotid sinus, the lungs, for bone healing, for pain control stimulators, and the like.

Objects and Advantages

Accordingly, it is an object of this invention to produce an implantable electric terminal for organic tissue which intermeshes with the tissue, and permits ingress of blood vessels without the production of a fibrous tissue interface that increases the stimulating threshold level.

Another object is to control the current density of an implantable electric terminal by increasing or decreasing the conductive surface area of such a terminal.

BRIEF DESCRIPTION OF THE VIEWS

The above mentioned and other features, objects and advantages, and a manner of obtaining them are described more specifically below by reference to embodiments of this invention shown in the accompanying drawings, wherein:

FIG. I is an enlarged perspective view of one embodiment of an electric terminal according to this invention; comprising a disk implanted on the surface of the tissue to be sensed or stimulated;

FIG. II is a further enlarged section taken along line II — II of FIG. I showing the separate electrically conductive and electrically non-conductive parts of this electric terminal;

FIG. III is an enlarged side view of a helical shaped electric terminal for insertion in a tissue, which terminal has a porous coating thereon.

FIG. IV is a further enlarged section taken along line IV — IV of FIG. III showing the porous coating surrounding the central electrically conductive part of the electric terminal.

FIG. V is a section similar to FIG. IV of another embodiment of this invention, in which the central electrically conductive part is porous also;

FIG. VI is a section similar to FIG. IV of a further embodiment of this invention in which the electrically non-conductive porous layer is plated with an electrically conductive material; and FIG. VII is a section similar to FIG. IV of still another embodiment of this invention, in which the outer porous portion is of the same electrically conductive material as the substrate.

DETAILED DESCRIPTION OF PREFERRED EMBODIMENTS

Referring first to FIGS. I and II, there is shown a disk-shaped electric terminal 10 implanted on organic tissue T, such as an epicardium. This electric terminal 10 is shown to have an electrically conductive metallic substrate or disk portion 12 into which may be axially threaded or soldered a similar metal conductor rod or wire 14 connected to an electrical sensor or stimulator circuit means 15 to which another electrode 10 by means of a conductor 14 is also connected to another portion of tissue T in the same body. On at least one of the flat surfaces 16 of the disk portion 12, and herein shown also around the periphery of the disk portion 12, is a layer of porous material 20. This porous material 20 is shown to be an electrically non-conductive ceramic material, such as aluminum oxide, containing a plurality of interconnected and continuous pores 22. Thus pores 22 fill with body electrolytes for conducting electricity between the disk 12 and the tissue T. Also into these pores 22 grow the blood capillaries C from the tissue T upon which the surface 24 of the disk 20 is intimately placed. This porous ceramic part 20 may be separately formed and then attached to the disk 12, or it may be sintered or integrally formed onto the disk 12.

Although this electric terminal 10 may be used either for electrically stimulating or sensing the tissue T, this electricity reaches the electrically conductive part 12 of this electric terminal 10 through the electrolyte in the pores 22 from the tissue T, and thence is conducted through the conductor or wire 14 out to the instrument 15 that generates or senses this electricity.

Referring now to the embodiment shown in FIGS. III and IV, the electrically conductive material or central wire portion 32 of the electric terminal 30 has an electrically non-conductive porous material coating or layer 40 thereon. This layer 40 may be separately formed and then a wire or post, such as the helical wire 32 threaded therein, or the porous layer 40 may be sintered or integrally formed onto the electrically conductive part 32. This porous layer 40 also has pores 42 that interconnect and are continuous so as to be permeable to body or tissue liquids from its outer surface inwardly to the electrically conductive part 32.

In the above described embodiments, the current density of the electric terminal 10 or 30 is relatively high since the only electrically conductive contact between the electrically conductive material 12 or 32 of the terminal is where the continuous pores 22 or 42 through the outer electrically non-conductive part open onto the outer surface 16 of the disk 12 or onto the outer surface of the center wire 32 for direct contact with the body electrolytes. In order to decrease this current density or increase the surface area of the electric terminal of this invention for contact with the body electrolytes in the body tissue T, the center electrically conductive part may be made porous also as shown in FIG. V, or the porous surrounding layer may be made of an electrically conductive material by being plated with a metal as shown in FIG. VI, or be made of an electrically conductive material different from or the same as or integrally with the center part as shown in FIG. VII.

Specifically, FIG. V shows a cross-section of an electric terminal 50 having an electrically non-conductive outer layer 60 with pores 62 and a center electrically conductive part 52 with pores 54 which fill with electrolyte from the tissue which passes through the pores 62.

Instead of or together with the embodiment shown in FIG. V, the outer porous layer 80 (see FIG. VI) of an implantable electric terminal 70 may be plated with a non-reacting metal or electrically conductive material 84 which plating also coats the surfaces of the continuous pores 82 so as to be in electrical contact with the electrically conductive center part 72, thereby increasing the current density of the electric terminal over that described in FIGS. II and III.

Rather than plating the electrically non-conductive porous layer of the electric terminal of this invention, this whole porous layer may be made of an electrically conductive material of a different part or the same composition as the electrically conductive center part; including forming the whole electric terminal out of the same material as shown in FIG. VII for the electric terminal 90 having an outer layer 100 with interconnected and continuous pores 102, and a center part 92, which center part may also be porous as shown in the embodiment of FIG. V.

It is to be understood that other shapes of the implantation electric terminals of this invention can be made embodying tissue compatible electrically conductive material having a porous layer thereon, which layer may be either separate or of the same material as the electrically conductive substrate of the electric terminal. Thus the disk shaped electric terminal 10 as shown in the embodiment in FIGS. I and II may have its porous disk part 20 formed of an electrically conductive material, such as shown in the embodiments of FIGS. V, VI, and/or VII, without departing from the scope of this invention.

Furthermore, the thickness of the porous layer may vary as desired, however, generally the dimensions of the electric terminal shown in FIGS. I and II have as their largest dimension about one centimeter, and as their smallest dimension, i.e. their thickness preferably less than about a quarter of a centimeter. Similarly, the electric terminals shown in FIGS. III through VII preferably have diameters less than about a quarter of a centimeter.

While there is described above the principles of this invention in connection with specific apparati, it is to be clearly understood that this description is made only by way of example and not as a limitation to the scope of this invention.

I claim:

1. A non-reacting implantable electric terminal for an organic tissue comprising: an electrically conductive portion having a surface thereof adapted to contact tissue electrolyte, said surface being completely surrounded and in intimate contact with an inert non-absorbable porous material having interconnected and continuous pores of an average diameter of between 10 and 500 microns so as to permit ingress of blood capillaries and intermeshing with said tissue without the formation of a fibrous tissue interface adjacent said surrounding part, and to permit electrolytes in the tissue to pass therethrough and to be in continuous contact with said electrically conductive portion, and means for connecting the electrically conductive portion of said electric terminal to an electrical circuit means.

2. An electric terminal according to claim 1 wherein said electrically conductive portion and said porous material are compatible with said electrolytes and said tissue.

3. An electric terminal according to claim 1 wherein said electrically conductive portion is an implantable metal.

4. An electric terminal according to claim 1 wherein said porous material comprises a ceramic metallic oxide.

5. An electric terminal according to claim 4 wherein said porous ceramic comprises aluminum oxide.

6. An electric terminal according to claim 1 wherein said porous material comprises a plastic.

7. An electric terminal according to claim 6 wherein said porous plastic is an elastomer.

8. An electric terminal according to claim 1 wherein said porous material comprises a mixture of a ceramic and plastic material.

9. An electric terminal according to claim 1 wherein said porous material is between about 5% and 85% porous.

10. An electric terminal according to claim 1 wherein said electrically conductive portion is substantially completely surrounded by said porous material.

11. An electric terminal according to claim 1 wherein said porous material is electrically conductive.

12. An electric terminal according to claim 1 wherein said electrically conductive portion and said porous material have substantially the same chemical composition.

13. An electric terminal according to claim 1 wherein said porous material forms a layer on said electrically conductive portion.

14. An electric terminal according to claim 1 wherein said electrically conductive portion is porous.

15. An electric terminal according to claim 1 wherein said porous material including its pores are coated with an electrically conductive material.

16. A non-reacting electric terminal for contact with organic tissue, comprising:
    a. a tissue compatible electrically conductive material having a surface thereof adapted to contact tissue electrolyte, and
    b. a porous layer of a tissue compatible inert non-absorbable material completely surrounding and in intimate contact with said surface of said conductive material, wherein at least some pores are interconnected through the thickness of said layer and have an average diameter ranging between about 10 and 500 microns,
    whereby blood vessels of said organic tissue can penetrate said pores without the formation of a fibrous tissue interface between said tissue and said materials adjacent said layer, and whereby electrolytes in said tissue can contact said electrically conductive material; and
    c. means for connecting the electrically conductive material of said electric terminal to an electrical circuit means.

17. An electric terminal according to claim 16 wherein said electrically conductive material is an implantable metal.

18. An electric terminal according to claim 16 wherein said porous material comprises a ceramic metallic oxide.

19. An electric terminal according to claim 18 wherein said porous ceramic comprises aluminum oxide.

20. An electric terminal according to claim 16 wherein said porous material comprises a plastic.

21. An electric terminal according to claim 16 wherein said porous layer is between about 5% and 85% porous.

22. An electric terminal according to claim 16 wherein said electrically conductive material is substantially completely surrounded by said porous layer of tissue compatible material.

23. An electric terminal according to claim 16 wherein said porous layer of material is electrically conductive.

24. An electric terminal according to claim 16 wherein said electrically conductive material and said porous layer of tissue compatible material have substantially the same chemical composition.

25. An electric terminal according to claim 16 wherein said electrically conductive material is porous.

26. An electric terminal according to claim 16 wherein said porous layer including its pores are coated with an electrically conductive material.

* * * * *